US 9,808,272 B2

(12) United States Patent
Wohl

(10) Patent No.: US 9,808,272 B2
(45) Date of Patent: Nov. 7, 2017

(54) TONSIL FORCEPS

(71) Applicant: Daniel L. Wohl, Jacksonville, FL (US)

(72) Inventor: Daniel L. Wohl, Jacksonville, FL (US)

( * ) Notice: Subject to any disclaimer, the term of this patent is extended or adjusted under 35 U.S.C. 154(b) by 0 days.

(21) Appl. No.: 14/866,900

(22) Filed: Sep. 26, 2015

(65) Prior Publication Data

US 2016/0015404 A1    Jan. 21, 2016

Related U.S. Application Data

(63) Continuation-in-part of application No. 13/450,985, filed on Apr. 19, 2012, now abandoned, which is a continuation of application No. 12/381,910, filed on Mar. 18, 2009, now abandoned.

(51) Int. Cl.
 *A61B 17/24* (2006.01)
 *A61B 17/28* (2006.01)

(52) U.S. Cl.
 CPC .......... *A61B 17/24* (2013.01); *A61B 17/282* (2013.01); *A61B 17/2833* (2013.01); *A61B 2017/2837* (2013.01)

(58) Field of Classification Search
 CPC ......... A61B 17/24; A61B 17/26; A61B 17/28; A61B 17/2804; A61B 17/2812; A61B 17/2816; A61B 17/282; A61B 17/2833; A61B 17/2841; A61B 17/29; A61B 2017/2837; A61B 2017/2911; A61B 2017/2926; A61B 2017/2927; A61B 2017/2945; A61B 2017/2946
 See application file for complete search history.

(56) References Cited

U.S. PATENT DOCUMENTS

| | | | |
|---|---|---|---|
| 2,257,288 A | 9/1941 | Trottier | |
| 2,340,995 A | 2/1944 | Smith | |
| 2,371,082 A | 3/1945 | Vistreich | |
| 2,583,892 A | 1/1952 | Shellhouse | |
| 2,668,538 A * | 2/1954 | Baker | A61B 17/12009 294/118 |
| 3,470,872 A | 10/1969 | Grieshaber | |
| 3,762,417 A | 10/1973 | Textor | |
| 5,059,214 A * | 10/1991 | Akopov | A61B 17/282 606/207 |
| 5,300,087 A * | 4/1994 | Knoepfler | A61B 17/29 604/33 |
| 5,693,069 A | 12/1997 | Shallman | |
| 5,893,878 A | 4/1999 | Pierce | |
| 6,099,539 A | 8/2000 | Howell et al. | |
| 6,156,009 A * | 12/2000 | Grabek | A61B 17/29 604/115 |
| 6,461,368 B2 | 10/2002 | Fogarty et al. | |
| 7,087,070 B2 | 8/2006 | Flipo | |
| 7,232,445 B2 | 6/2007 | Kortenbach et al. | |
| 2003/0144693 A1 | 7/2003 | Flipo | |

(Continued)

*Primary Examiner* — Jocelin Tanner
(74) *Attorney, Agent, or Firm* — Thomas C. Saitta

(57) ABSTRACT

A locking tonsil forceps having first and second intersecting and pivoting arm members, and grasping members disposed on the arm members. The grasping members have blunt tine members, a concave interior surface, inwardly facing blunt interior projection members, flush lateral projection members and angled lateral projection members. The tine members and projecting members are non-contacting with each other even in the maximum closed forceps position.

20 Claims, 18 Drawing Sheets

(56) References Cited

U.S. PATENT DOCUMENTS

2008/0300622 A1 12/2008 Xu
2009/0131933 A1\* 5/2009 Ghabrial ............ A61B 18/1445
 606/51

\* cited by examiner

TONSIL FORCEPS

This application is a continuation-in-part of U.S. patent application Ser. No. 13/450,985, filed Apr. 19, 2012, which is a continuation-in-part of U.S. patent application Ser. No. 12/381,910, filed Mar. 18, 2009, claiming the benefit of U.S. Provisional Patent Application Ser. No. 61/069,942, filed Mar. 18, 2008.

BACKGROUND OF THE INVENTION

This invention relates generally to the field of medical forceps, and more particularly to such forceps that are lockable in multiple indexed closure positions and that possess distal end finger-like projections.

Forceps are handheld instruments in the form of tongs or pincers used to grasp, compress or pull body parts, tissue, organs, teeth, etc. A typical forceps comprises a pair of pivotally joined elongated arm members, the proximal ends of the arms being provided with finger holes for manipulating the instrument and the distal ends being provided with grasping structures suited for particular purposes, such as finger-like extensions, sharp teeth, blades, curved members, concave members, etc. Many forceps are provided with releasable locking means, such as for example a pair of opposing toothed bar members, one mounted on each arm and extending toward each other, that together act in a ratcheting manner, whereby the forceps will remain in a set clamping or spread position without the need for the surgeon physically maintaining a handhold, and whereby the forceps can be released from the locked position by separating the toothed bar members in the directions of the pivot axis.

In the removal of tonsils, it is necessary to grasp and pull the tonsil in order to separate and resect the tonsil from the surrounding mucosa, muscle and fascia. By pulling on the tonsil the anatomy surrounding the tonsil and the edges of the tonsil itself are better exposed, and the surgeon is able to more carefully cut into the tissue. Often the tonsils are partially embedded within the muscles and fascia, such that grasping the tonsil is difficult. The current style forceps used for this task tend to bite, stab or cut the tonsil during this grasping operation, resulting in undesirable fragmentation of the tonsil during the resection.

It is an object of this invention to provide tonsil forceps that alleviate the problems encountered with standard forceps such that the tonsil may be grasped and pulled without biting into, cutting, stabbing or otherwise excessively piercing the surface or fragmenting the tonsil during resection. It is an object to provide such tonsil forceps wherein the distal grasping members comprise a pair of human palm-like segments that are curved toward each other, each having tine members that are interdigitating when the forceps are fully closed. It is a further object to provide such tonsil forceps wherein inwardly facing projection members are provided on the grasping members of the elongated arm members in order to better grasp the tonsil. It is a further object to provide such tonsil forceps having interior projection members and two sets of laterally mounted projection members, one set being oriented flush with the sides of the grasping members and the other set being oriented at an outward angle to extend away from the sides of the grasping members. It is a further object to provide such tonsil forceps wherein the interior projection members are structured so as to prevent shearing of the tonsil when grasped. It is a further object to provide such tonsil forceps wherein releasable locking means are provided such that the forceps may be locked into at least one position in which the tips of the finger-like tines are not interdigitated.

SUMMARY OF THE INVENTION

The invention is a tonsil forceps comprising first and second intersecting and pivoting arm members, the arm members being joined by pivoting connection means at an intermediate point such that the distal ends of the forceps can be closed for grasping and opened for release in a scissoring manner by relative movement of the proximal ends toward and away from each other, respectively. The pivoting connection defines a pivot plane. Releasable locking means for securing the forceps in multiple locked positions are provided, such as for example a ratchet-type mechanism. Finger loops are provided on the proximal ends of the arm members. Each of the distal ends of the arm members comprises grasping members for securing a tonsil, with each grasping member being a widened curved portion that is curved toward the other grasping member. In addition, the grasping members are angled or bent out of the pivot plane to define a distal end concave side and a distal end convex side.

In one aspect or embodiment, the each grasping member is provided with a set of inwardly curved, blunt tipped, finger-like tine members extending generally inwardly toward the other set of tine members, wherein the sets of finger-like tine members of one distal end pass between but do not contact the finger-like tine members of the other distal end when the forceps are closed. In at least one of the locked positions, the tips on one set of the finger-like tines do not cross the tips of the other set of finger-like tines. The grasping means further comprise inwardly facing projection members, some of said projection members being disposed on the interior of the grasping members and formed in the shape of for example raised ridges, blunted teeth, posts, nubs or the like. Additional projection members in the form of relatively sharp teeth are disposed on the sides or lateral edges of the palm-like portions, one set being oriented flush with the sides of the palm-like segments and the other set being oriented at an outward angle to extend away from the sides of the palm-like segments. The projection members are non-contacting with each other even in the maximum closed forceps position.

In an alternative aspect or embodiment the invention is a tonsil forceps comprising a first intersecting arm member and a second intersecting arm member, each having a distal end and a proximal end, said arm members being joined by pivoting connection means defining a pivot plane, such that said distal ends can be closed and opened by bringing together or spreading apart said arm member proximal ends in scissor-like manner, said distal ends of said arm members extending out of said pivot plane whereby each said arm member has a concave side and a concave side; a finger loop positioned at said proximal end of each said arm member; each of said distal ends comprising means for grasping a tonsil to separate said tonsil from surrounding mucosa, muscle and fascia, each said grasping means comprising a grasping member comprising a concave interior surface bounded by a convex-side lateral edge and a concave-side lateral edge, a set of tine members extending generally in the distal direction with gaps between said tine members, whereby said tine members of said first arm member and said tine members of said second arm member are interdigitated when the forceps are fully closed, and inwardly facing, blunt projection members positioned on each of said interior surfaces, wherein said blunt projection members do not contact each other when said forceps is fully closed; said grasping means further comprising at least one flush lateral projection member disposed on or adjacent said concave-side lateral edge and at least one angled lateral projection member disposed on or adjacent said convex-side lateral edge, whereby said at least one flush lateral projection member is flush with said concave side and said at least one angled projection member extends outwardly from said convex side; means for temporarily locking said forceps in a fixed position, wherein said locking means comprise a first transverse bar member mounted to said first arm member and a second transverse bar member mounted to said second arm member, said transverse bar members being inwardly facing and opposing, such that said transverse bar members slidingly engage as said forceps are closed, said locking means further comprising opposing teeth members positioned on said transverse bar members, and further wherein said locking means provides at least one locked position wherein said tine members are not interdigitized. This embodiment may further comprise at least one ridge extending across said interior surface of said grasping member; may further comprise means for pivoting said arm members comprising an intermediate body segment disposed on each said arm member, each said intermediate body segment having a flat interface surface and a bore, and a mechanical fastener positioned in said bore; may further comprise pointed lateral projection members and pointed angled lateral projection members; and said flush lateral projection members may extend approximately 90 degrees from said interior surface and said angled lateral projection members extend approximately 135 degrees from said interior surface.

In a more preferred embodiment of the alternative embodiment, the tine members continue a short distance along the convex sides of the grasping members, and the inwardly facing blunt projection members of one grasping member are not aligned but are instead offset from the inwardly facing blunt projection members of the other grasping member. The blunt projection members of each grasping member are non-parallel, such that the distal blunt projection members are wider apart than the proximal blunt projection members.

In alternative terms, the preferred embodiment is a tonsil forceps comprising a first intersecting arm member and a second intersecting arm member, each having a distal end and a proximal end, said arm members being joined by pivoting connection means defining a pivot plane, such that said distal ends can be closed and opened by bringing together or spreading apart said arm member proximal ends in a scissor-like manner, said distal ends of said arm members extending out of said pivot plane such that each said arm member has a concave side and a convex side; a finger loop positioned at said proximal end of each said arm member; means for temporarily locking said forceps in a fixed position; each said first and said second arm members comprising a tonsil grasping member, each said grasping member comprising an interior surface bounded by a convex-side lateral edge and a concave-side lateral edge, tine members positioned on said distal end and extending around onto said convex-side edge of each grasping member, tine gaps disposed between said tine members, inwardly facing, interior projection members positioned on each of said interior surfaces, and projection gaps disposed between said interior projection members; wherein said tine members of said first arm member are positioned opposite from said tine gaps of said second arm member and said tine members of said second arm member are positioned opposite said tine gaps of said first arm member, such that said tine members do not contact each other when said forceps are closed; wherein said interior projection members of said first arm member are positioned opposite from said projection gaps of said second arm member and said interior projection members of said second arm member are positioned opposite said projection gaps of said first arm member, such that said interior projection members do not contact each other when said forceps are closed; and each said grasping member further comprising at least one flush lateral projection member disposed on or adjacent said concave-side lateral edge and at least one angled lateral projection member disposed on or adjacent said convex-side lateral edge, whereby said at least one flush lateral projection member is flush with said concave side and said at least one angled projection member extends outwardly from said convex side. Furthermore, such forceps wherein said tine members comprise flat surfaces with ridges; wherein said interior projection members comprise flat surfaces with ridges; wherein said tine members comprise flat surfaces with ridges; wherein said interior projection members are provided in two laterally-extending sets on each said grasping member, ones said set being a distal set and the other said set being a proximal set; wherein each said set of said interior projection members positioned on said first arm member comprises three interior projection members and two projection gaps, and wherein each said set of said interior projection members positioned on said second arm member comprises two interior projection members and one projection gap; wherein each said set of said interior projection members positioned on said first arm member is V-shaped; wherein each of said projection gaps of each said distal set of said interior projection members on said first arm member align with said projection gaps of each said proximal set of interior projection members; wherein the middle interior projection member of each said set of said interior projection members on said first arm member is wider than the outer interior projection members of each said set of said interior projection members on said first arm member; wherein on said first arm member, the flat surfaces of said tine members and said interior projection members lie in the same plane, and wherein on said second arm member, the flat surfaces of said tine members and said interior projection members lie in the same plane; wherein said flush lateral projection members extend approximately 90 degrees from said interior surface and said angled lateral projection members extend approximately 135 degrees from said interior surface; and/or wherein said flush lateral projection members and said angled lateral projection members are pointed.

Alternatively, a preferred embodiment for a tonsil forceps comprising a first intersecting arm member and a second intersecting arm member, each having a distal end and a proximal end, said arm members being joined by pivoting connection means defining a pivot plane, such that said distal ends can be closed and opened by bringing together or spreading apart said arm member proximal ends in a scissor-like manner, said distal ends of said arm members extending out of said pivot plane such that each said arm member has a concave side and a convex side; a finger loop positioned at said proximal end of each said arm member; means for temporarily locking said forceps in a fixed position; each said first and said second arm members comprising a tonsil grasping member, each said grasping member comprising an interior surface bounded by a convex-side lateral edge and a concave-side lateral edge, flat surfaced tine members positioned on said distal end and extending around onto said convex-side edge of each grasping member, tine gaps disposed between said tine members, inwardly facing, flat surfaced interior projection members positioned on each of said interior surfaces, and projection gaps disposed between said interior projection members; wherein said tine members of said first arm member are positioned opposite from said tine gaps of said second arm member and said tine members of said second arm member are positioned opposite said tine gaps of said first arm member, such that said tine members do not contact each other when said forceps are closed; wherein said interior projection members of said first arm member are positioned opposite from said projection gaps of said second arm member and said interior projection members of said second arm member are positioned opposite said projection gaps of said first arm member, such that said interior projection members do not contact each other when said forceps are closed; and each said grasping member further comprising at least one flush lateral projection member disposed on or adjacent said concave-side lateral edge and at least one angled lateral projection member disposed on or adjacent said convex-side lateral edge, whereby said at least one flush lateral projection member is flush with said concave side and said at least one angled projection member extends outwardly from said convex side, said at least one flush lateral projection member and said at least one angled lateral projection member being pointed. Furthermore, such forceps wherein said tine members and said interior projection members comprise ridges; wherein on said first arm member, the flat surfaces of said tine members and said interior projection members lie in the same plane, and wherein on said second arm member, the flat surfaces of said tine members and said interior projection members lie in the same plane; wherein said flush lateral projection members extend approximately 90 degrees from said interior surface and said angled lateral projection members extend approximately 135 degrees from said interior surface; wherein on said first arm member, the flat surfaces of said tine members and said interior projection members lie in the same plane, and wherein on said second arm member, the flat surfaces of said tine members and said interior projection members lie in the same plane; wherein said interior projection members are provided in two laterally-extending sets on each said grasping member, ones said set being a distal set and the other said set being a proximal set; wherein each said set of said interior projection members positioned on said first arm member comprises three interior projection members and two projection gaps, and wherein each said set of said interior projection members positioned on said second arm member comprises two interior projection members and one projection gap; wherein each said set of said interior projection members positioned on said first arm member is V-shaped; and wherein each of said projection gaps of each said distal set of said interior projection members on said first arm member align with said projection gaps of each said proximal set of interior projection members; and/or wherein the middle interior projection member of each said set of said interior projection members on said first arm member is wider than the outer interior projection members of each said set of said interior projection members on said first arm member.

Still further alternatively, a tonsil forceps comprising a first intersecting arm member and a second intersecting arm member, each having a distal end and a proximal end, said arm members being joined by pivoting connection means defining a pivot plane, such that said distal ends can be closed and opened by bringing together or spreading apart said arm member proximal ends in a scissor-like manner, said distal ends of said arm members extending out of said pivot plane such that each said arm member has a concave side and a convex side; a finger loop positioned at said proximal end of each said arm member; means for temporarily locking said forceps in a fixed position; each said first and said second arm members comprising a tonsil grasping member, each said grasping member comprising an interior surface bounded by a convex-side lateral edge and a concave-side lateral edge, flat surfaced tine members positioned on said distal end and extending around onto said convex-side edge of each grasping member, tine gaps disposed between said tine members, inwardly facing, flat surfaced interior projection members positioned on each of said interior surfaces, and projection gaps disposed between said interior projection members; wherein said tine members of said first arm member are positioned opposite from said tine gaps of said second arm member and said tine members of said second arm member are positioned opposite said tine gaps of said first arm member, such that said tine members do not contact each other when said forceps are closed; wherein on said first arm member, the flat surfaces of said tine members and said interior projection members lie in the same plane, and wherein on said second arm member, the flat surfaces of said tine members and said interior projection members lie in the same plane; wherein said interior projection members of said first arm member are positioned opposite from said projection gaps of said second arm member and said interior projection members of said second arm member are positioned opposite said projection gaps of said first arm member, such that said interior projection members do not contact each other when said forceps are closed; wherein said interior projection members are provided in two laterally-extending sets on each said grasping member, ones said set being a distal set and the other said set being a proximal set; wherein each said set of said interior projection members positioned on said first arm member comprises three interior projection members and two projection gaps, and wherein each said set of said interior projection members positioned on said second arm member comprises two interior projection members and one projection gap; wherein each said set of said interior projection members positioned on said first arm member is V-shaped; and wherein each of said projection gaps of each said distal set of said interior projection members on said first arm member align with said projection gaps of each said proximal set of interior projection members; wherein the middle interior projection member of each said set of said interior projection members on said first arm member is wider than the outer interior projection members of each said set of said interior projection members on said first arm member; and each said grasping member further comprising at least one flush lateral projection member disposed on or adjacent said concave-side lateral edge and at least one angled lateral projection member disposed on or adjacent said convex-side lateral edge, whereby said at least one flush lateral projection member is flush with said concave side and said at least one angled projection member extends outwardly from said convex side, said at least one flush lateral projection member and said at least one angled lateral projection member being pointed, and wherein said flush lateral projection members extend approximately 90 degrees from said interior surface and said angled lateral projection members extend approximately 135 degrees from said interior surface.

DETAILED DESCRIPTION OF THE INVENTION

Figure 1:
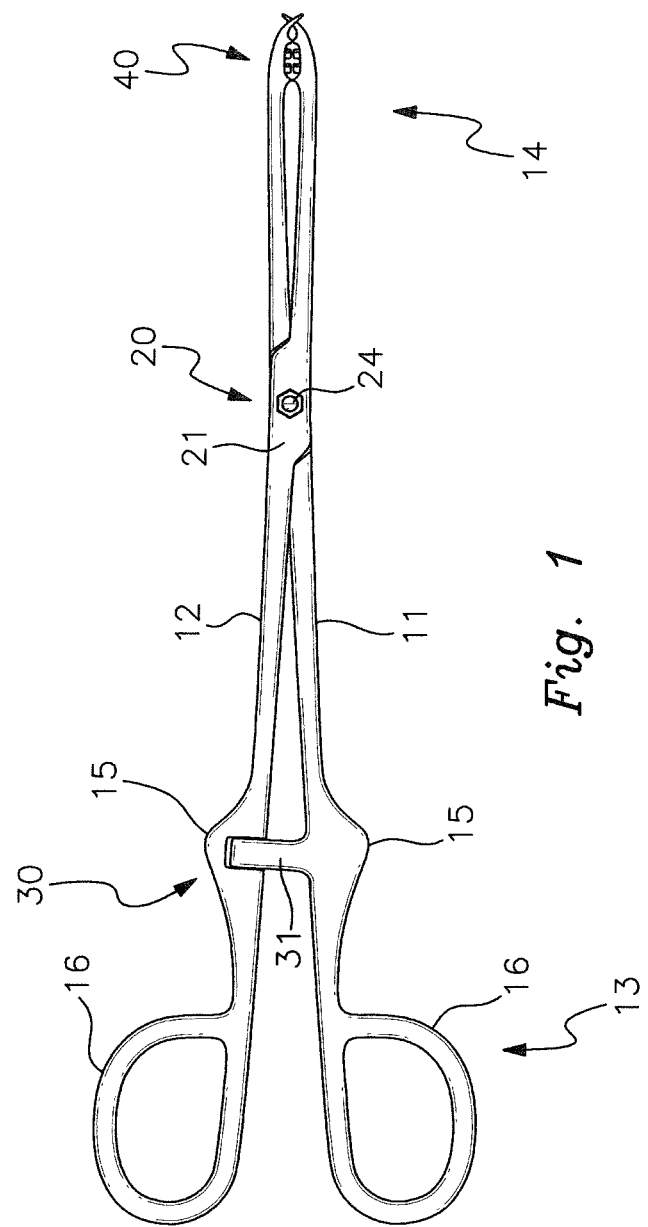
FIG. 1 is a plan view of one embodiment of the tonsil forceps shown in the fully closed, locked orientation, wherein the finger-like projection members are interdigitized and pass by each other without contact.
Figure 2:
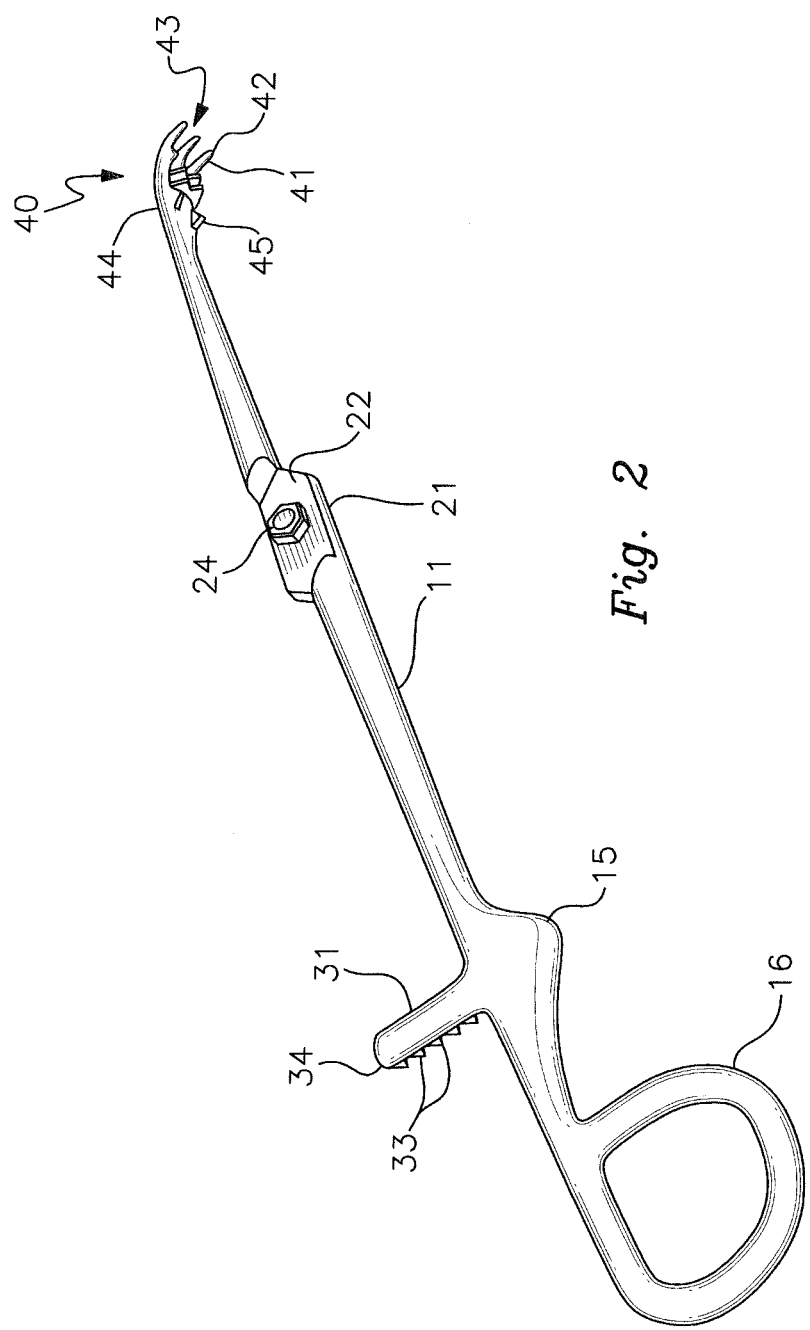
FIG. 2 is a perspective view of one of the pivoting arm members of the embodiment of FIG. 1.
Figure 3:
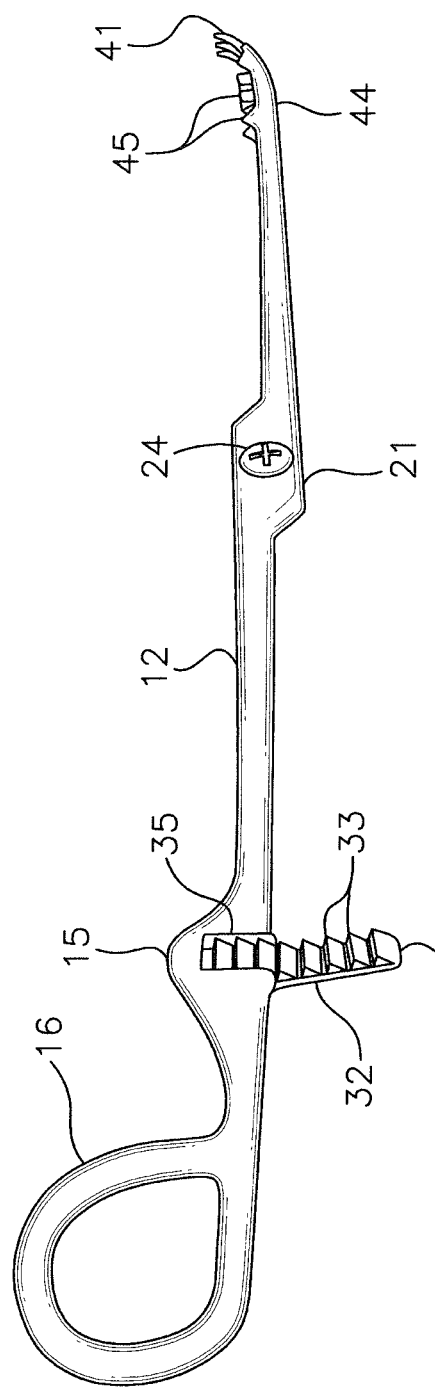
FIG. 3 is a perspective view of the other arm member of the embodiment of FIG. 1.
Figure 4:
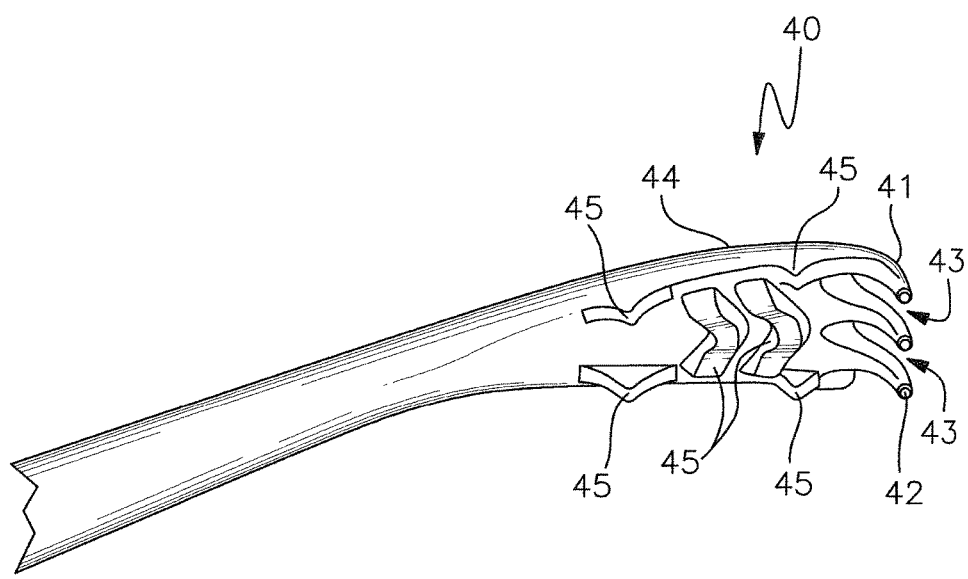
FIGS. 4 and 5 are perspective views of the distal end of one of the arm members of the embodiment of FIG. 1.
Figure 5:
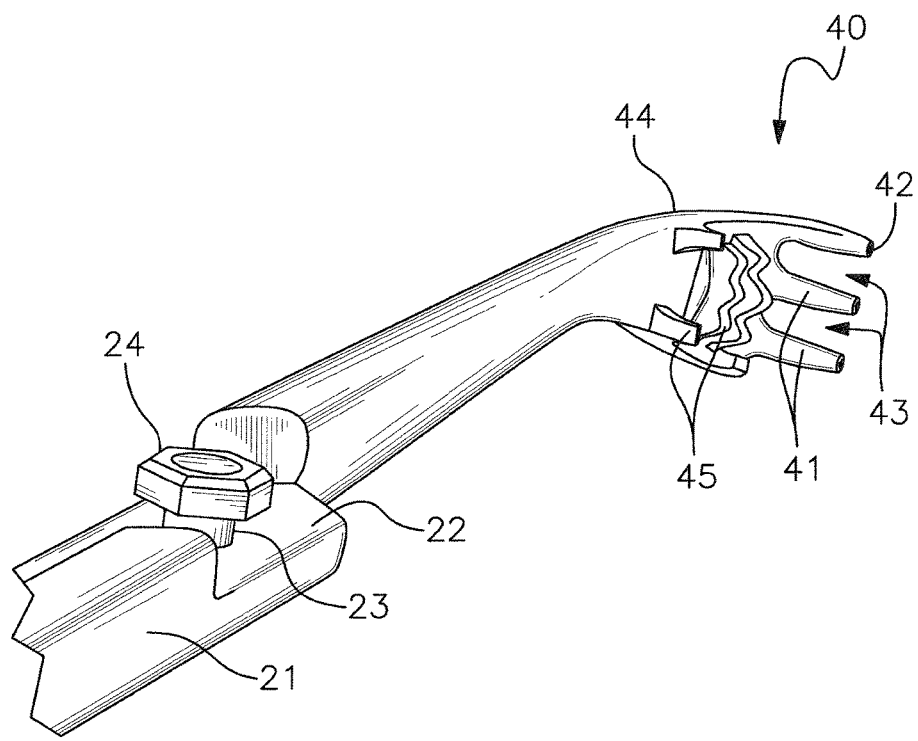

With reference to the drawings, the invention will now be described in detail with regard for the best mode and the preferred embodiment. In a most general sense, the invention is a tonsil forceps for grasping or pulling a tonsil so as to separate it from the surrounding mucosa, muscle and fascia, the structure of the grasping means being such that the tonsil is cradled rather than stabbed or cut by the grasping means during removal, and therefore remains intact as opposed to being fragmented during the resection procedure. The tonsil forceps may be realized in various embodiments.

A first embodiment of the tonsil forceps is illustrated in FIGS. 1 through 6. The tonsil forceps comprise a first intersecting arm member 11 and a second intersecting arm member 12, each having a distal end 13 and a proximal end 14. The arm members 11 and 12 are connected by means 20 for pivoting the arm members 11 and 12, such that the distal ends 13 of the arm members 11 and 12 can be closed and opened by bringing together or spreading apart the arm member proximal ends 14 in scissor-like manner. The pivoting connection means 20 may comprise for example the combination of an intermediate body segment 21 disposed on each arm member 11 and 12, the intermediate body segment 21 having a flat interface surface 22 that promotes rotational sliding movement between the arm members 11 and 12. A bore 23 is provided through the intermediate body segments 21 and a mechanical fastener 24, such as a nut and bolt in combination, is positioned in the bore 23. The pivoting means 20 defines a pivot plane. Preferably, the distal ends 13 of the arm members 11 and 12 are angled slightly, approximately 10 to 30 degrees, out of the pivot plane.

The proximal ends 13 of the arm members 11 and 12 comprise or are defined by finger loops 16. Thumb flanges 15 to aid in manipulating the tonsil forceps and releasing the locking means 30 may be disposed on the arm members 11 and 12. The tonsil forceps are provided with releasable locking means 30 for temporarily locking or securing the forceps in a fixed position such that that the locking means 30 must be released in order to open or close the forceps. The releasable locking means 30 may comprise for example a first transverse bar member 31 mounted to the first arm member 11 and a second transverse bar member 32 mounted to the second arm member 12. The transverse bar members 31 and 32 are inwardly facing and opposing, such that they slidingly engage as the forceps are opened and closed. Opposing ratchet-like teeth or ridge members 33 are positioned on the opposing surfaces of the transverse bar members 31 and 32, and the transverse bar members 31 and 32 preferably have beveled ends 34 so that they more readily slide across each other at initial closure. The transverse bar members 31 and 32 are preferably located at or near the thumb flanges 15 for ease of disengagement, and the thumb flanges 15 may be provided with slots 35 to receive the transverse bar members 31 and 32 when the forceps are fully closed. Typically, the teeth members 33 are configured with angled surfaces whereby the teeth members 33 present only minimum resistance when the forceps are closed, yet readily retain the forceps in a locked orientation when pressure is no longer applied. To open the forceps, each arm member 11 and 12 is moved in a direction perpendicular to the closure plane, such that the transverse bar members 31 and 32 are spread apart and the teeth 33 no longer are in contact. Such mechanisms are well known in the art.

Figure 6:
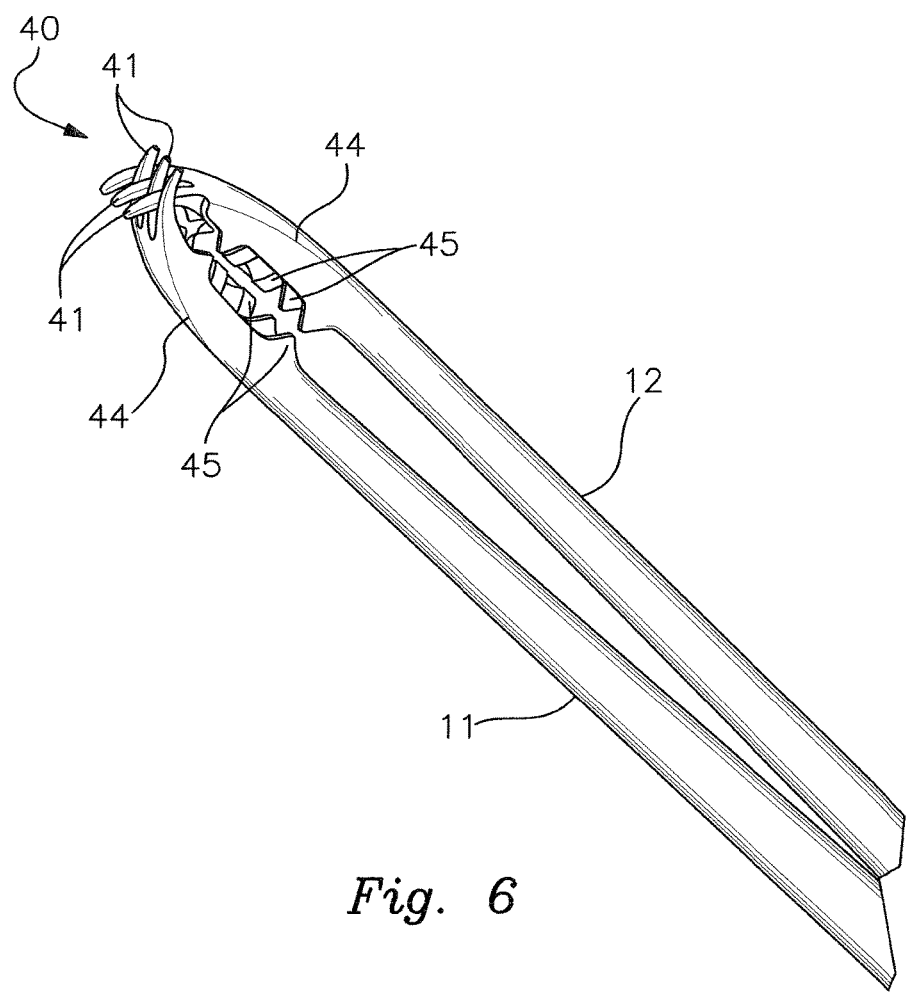
FIG. 6 is a perspective view of the distal ends of the arm members of the embodiment of FIG. 1 in the fully closed, locked orientation, wherein the finger-like projection members are interdigitized and pass by each other without contact.
Figure 7:
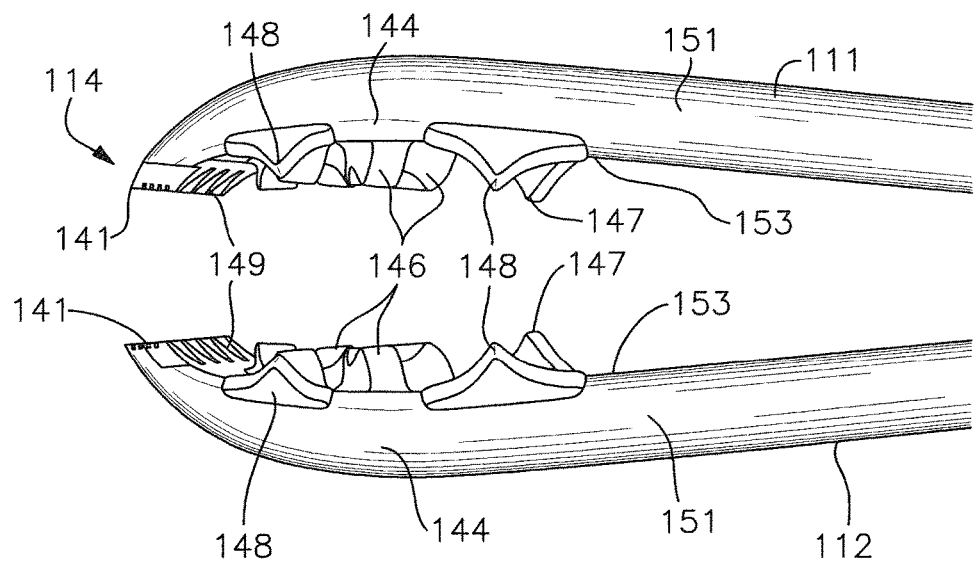
FIG. 7 is a partial lateral view of the distal ends of the arm members of an alternative embodiment of the tonsil forceps in an open position, shown from the convex side.
Figure 8:
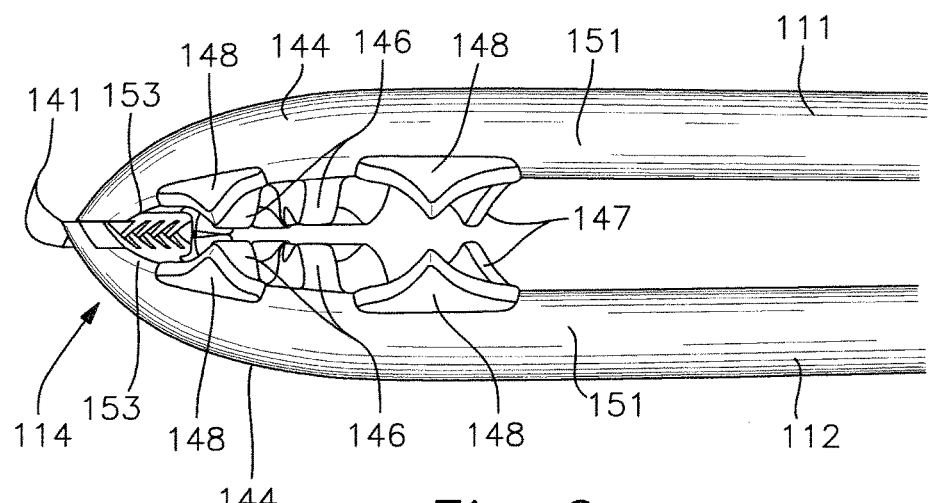
FIG. 8 is a partial lateral view of the distal ends of the arm members of the embodiment of FIG. 7, shown from the convex side with the arm members in the fully closed position.
Figure 9:
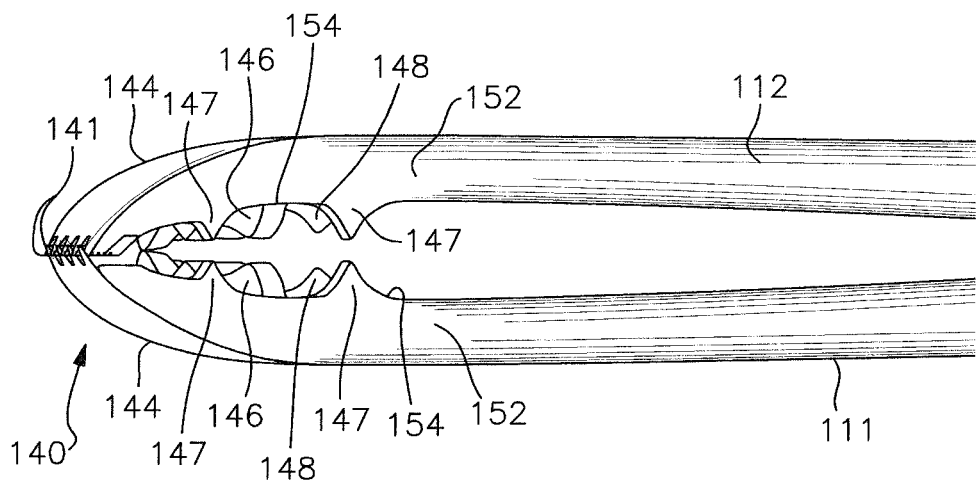
FIG. 9 is a partial lateral view of the distal ends of the arm members of the embodiment of FIG. 7, shown from the concave side with the arm members in the fully closed position.
Figure 10:
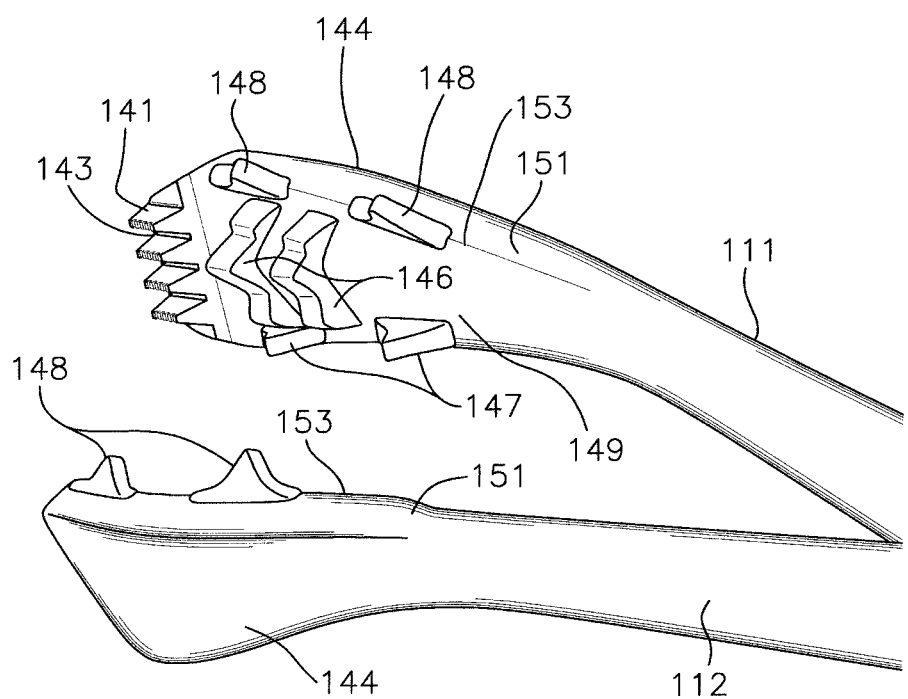
FIG. 10 is a partial perspective view of the distal ends of the arm members of the embodiment of FIG. 7, shown from the convex side with the arm members in an open position.
Figure 11:
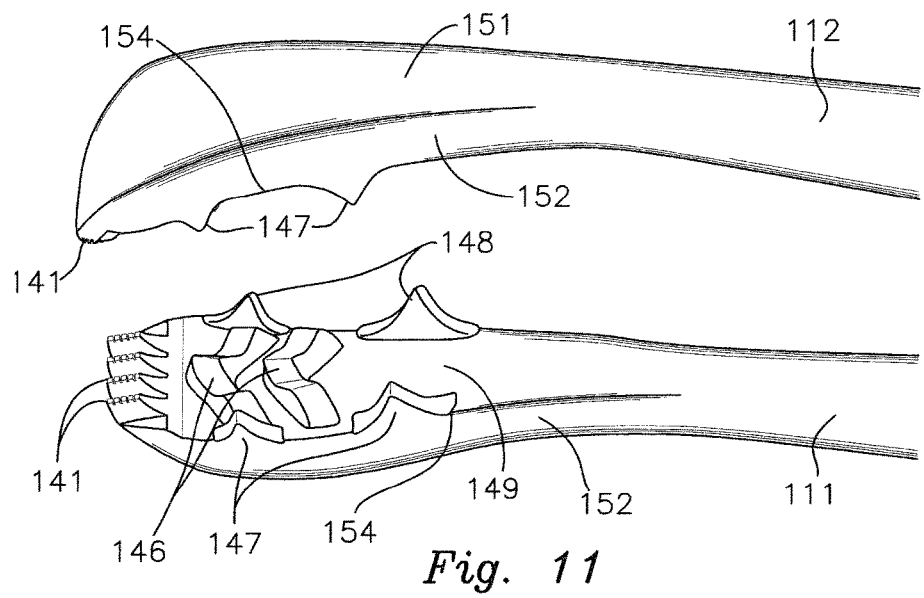
FIG. 11 is a partial perspective view of the distal ends of the arm members of the embodiment of FIG. 7, shown from the concave side with the arm members in an open position.
Figure 12:
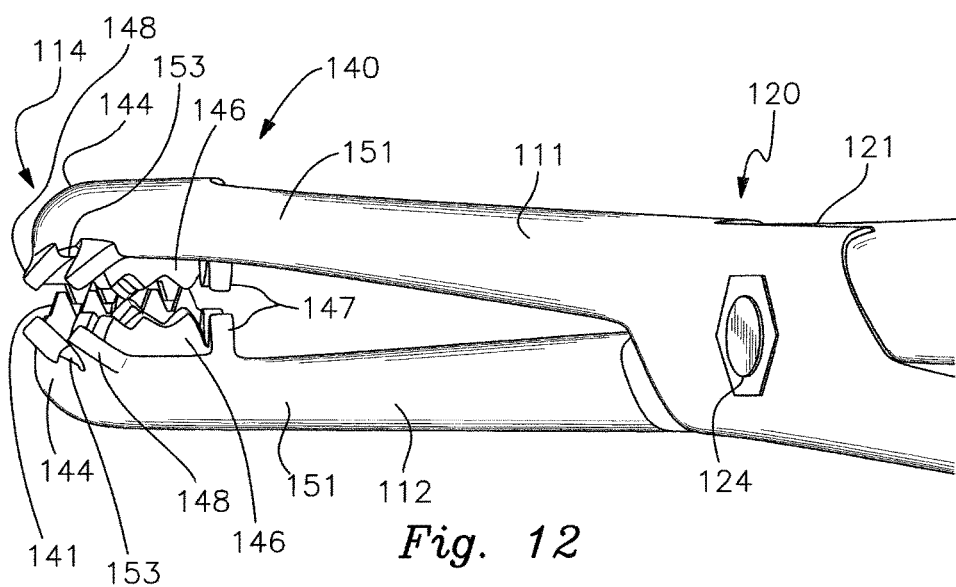
FIG. 12 is a partial perspective view of the distal ends of the arm members of the embodiment of FIG. 7, shown from the convex side with the arm members in the fully closed position.
Figure 13:
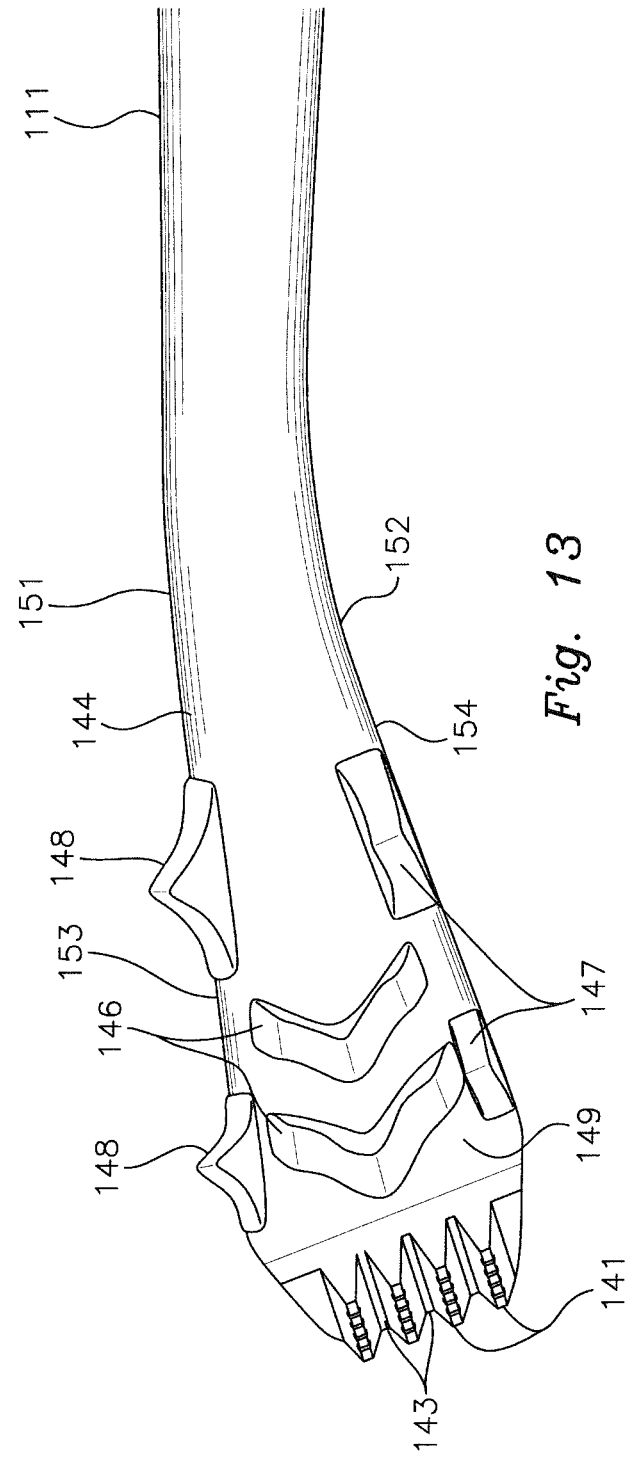
FIG. 13 is a plan view of the distal end of one of the arm members of the embodiment of FIG. 7.
Figure 14:
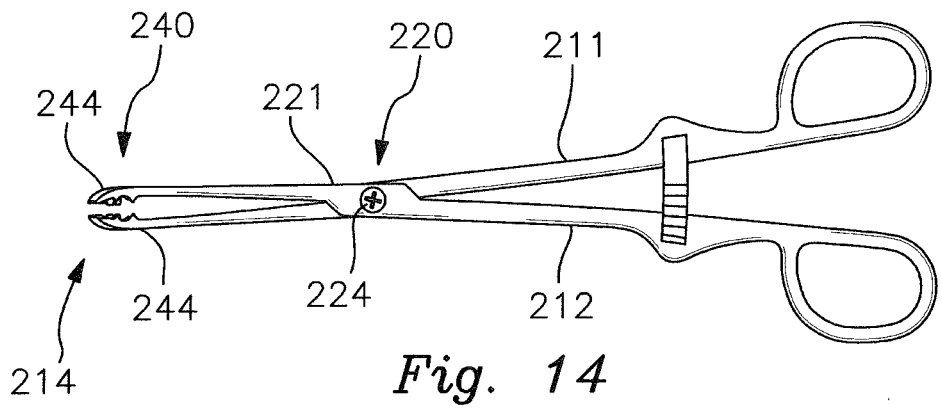
FIG. 14 is a plan view of still another alternative embodiment of the tonsil forceps shown in a partially open, locked configuration.
Figure 15:
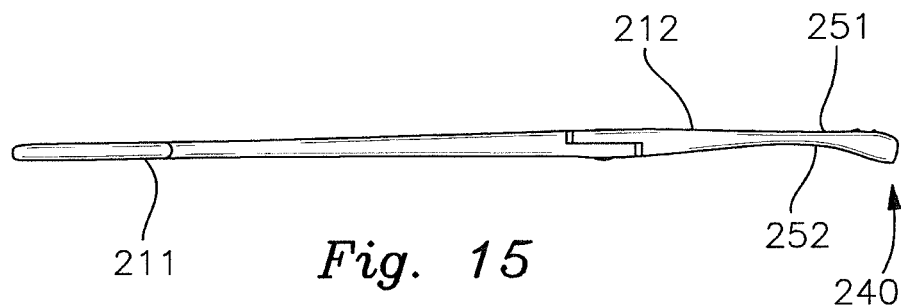
FIG. 15 is a lateral view of the embodiment of FIG. 14.
Figure 16:
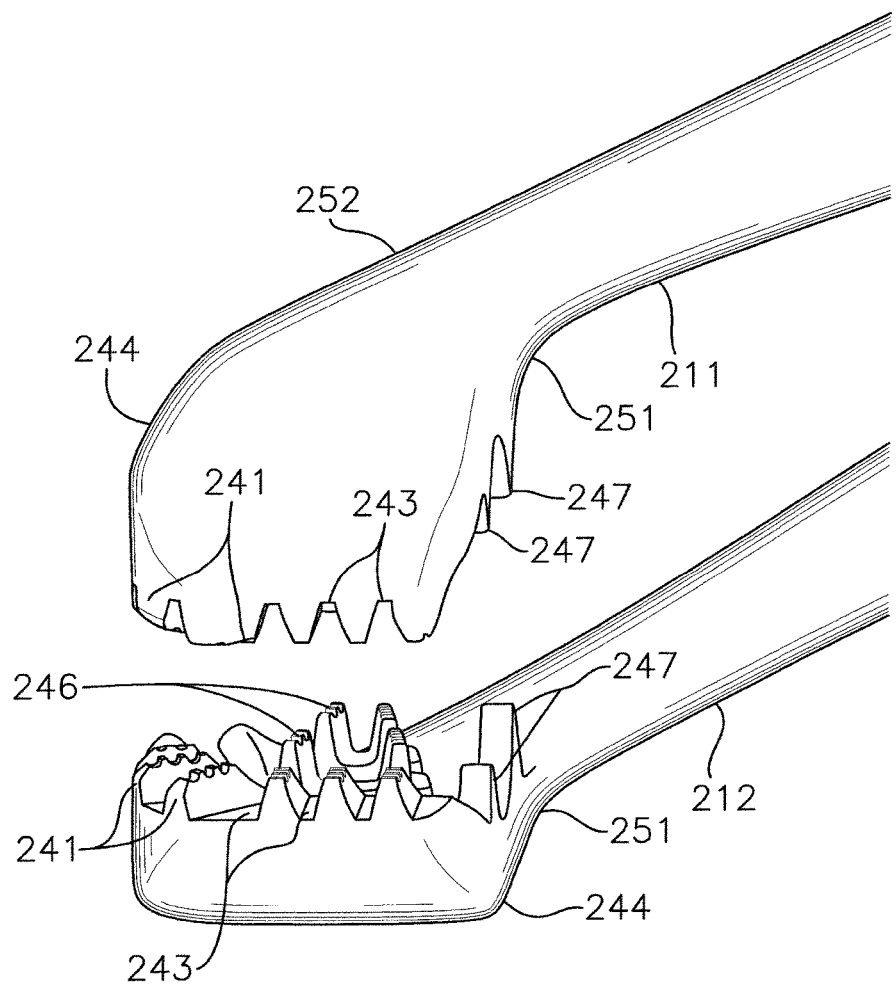
FIG. 16 is a partial perspective view of the distal ends of the embodiment of FIG. 14, shown from the concave side.

The distal end 14 of the tonsil forceps comprises or defines grasping means 40 for grasping, cradling, securing and pulling a tonsil to separate the tonsil from the mucosa, muscle and fascia. The grasping means 40 comprise a set of human-finger-like tine members 41 extending generally in the distal direction from a relatively broad, human-palm-like curved portion 44 located on each arm member 11 and 12, with broad curved portions 44 being inwardly concave. The finger-like tine members 41 are inwardly curved with blunt tips 42 and are separated by gaps 43, with the tines 41 preferably tapering toward the blunt tips 42. Each set of the tine members 41 is structured so as to be non-contacting and non-shearing with the other set of tine members 41 when the forceps are closed and the tines 41 are fully interdigitated, i.e., when the two sets of tips 42 intersect and pass by each other and the finger-like tines 41 pass into the gaps 43. Furthermore, it is most preferable that in at least one locked position, i.e., a first lock or click position, the tine members 41 are not interdigitated or intersecting, i.e., the tips 42 of the two sets of tine members 41 are disposed on opposite sides of an imaginary plane located between the distal ends 14 of the first and second arm members 11 and 12. As the forceps are more fully closed, the tips 42 will cross the imaginary plane such that the tips 42 extend through the gaps 43 outwardly beyond and away from the opposing set of tine members 41, as shown in FIG. 6. As previously stated, it is critical that the tine members 41 do not make any contact, such that any scissoring or shearing action is precluded during closure of the forceps.

Preferably, the inner sides of the palm-like curved portions 44 have inwardly facing projection members 45 located thereon, the projection members 45 being blunt structural features, such as raised ridges, mounds, posts or the like which will abut the sides of the tonsil but not penetrate or cut into its surface when the forceps are closed around the tonsil. The projection members 45 better secure the tonsil during the grasping and pulling motions of the resection, and the surfaces of the projection members 45 may be roughened to provide better traction. The projection members 45 are sized and positioned such the projection members 45 of opposing palm-like curved segments 44 do not touch when the forceps are in the fully closed position.

In a representative and non-limiting exemplar embodiment of the invention, the following dimensions, all being approximate, are provided as suitable. The forceps may have an overall length of 21.5 cm with the pivoting connection means 20 centered 7 cm from the distal end 14 and the releasable locking means 30 positioned 8 cm from the pivoting connection means 20. In the first lock position, there is a 1.2 cm gap between the tips 42 of the finger-like tine members 41 and an exterior dimension of 1.7 cm at the widest points on the palm-like curved portions 44. In the fully closed position, interior sides of the palm-like curved portions 44 are separated 5 mm and the projection members 45 are separated 1.5 mm, with the finger-like tine members 41 overlapped 1.5 mm. Preferably the distal ends 13 of the forceps containing the palm-like curved portions 44 and the finger-like tine members 41 are disposed approximately 22 degrees out of plane from the arm members 11 and 12, and the overall length of the palm-like curved portions 44 and the finger-like tine members 41 is 1.75 cm, with the finger-like tine members 41 extending 2.5 mm beyond the palm-like curved portions 44. The maximum height of the projection members 45 is 1.375 mm. As shown in the drawings, the projection members 45 may comprise a plurality of undulating ridge members extending transversely across the palm-like curved portion 44 and a plurality of blunt tooth members positioned adjacent the sides of the palm-like curved portion 44.

A second and alternative embodiment of the tonsil forceps is illustrated in FIGS. 7 through 13. The structure and elements of the proximal portion of the tonsil forceps of this embodiment are identical or functionally similar to the proximal structure and elements of the first embodiment described herein. This second embodiment comprises first and second intersecting arm members 111 and 112 that are joined by pivoting connection means 120, such as a mechanical fastener 124 pivotally joining opposing intermediate body sections 121 in a manner that allows for scissor-type relative motion, the pivoting connection means 120 thereby defining a pivot plane. The portions of the first and second intersecting arm members 111 and 112 adjacent the distal end 114 of the tonsil forceps extend from the defined pivot plane, such that each of the first and second intersecting arm members have a convex side 151 and a concave side 152. In other words, with the tonsil forceps placed onto a planar surface, the distal portions of the first and second intersecting arm members 111 and 112 will angle upward and extend out of the planar surface.

The distal portions of the first and second intersecting arm members 111 and 112 extending from the pivot plane define the grasping means 140 which are comprised of grasping members 144, the grasping members 144 being relatively wide and thin in cross-section members that are curved out of the pivot plane. The opposing interior surfaces 149 of the grasping members 144 are concavely curved, such that an open tonsil-receiving area is defined between the opposing interior surfaces 149, and each opposing interior surface 149 is laterally bounded by a convex-side lateral edge 153 (i.e., a lateral edge located on the convex side 151) and a concave-side lateral edge 154 (i.e., a lateral edge located on the concave side 152). The lateral edges 153 and 154 may be straight, angled, curved or curvi-linear. The distal ends of the grasping members 144 each comprise a plurality of relatively short teeth or tine members 141 separated by gaps 143, the tine members 141 and gaps 143 structured such that with the intersecting arm members 111 and 112 in the fully closed position, the tine members 141 of the first intersecting arm member 111 fit into the gaps 112 of the second intersecting arm member 112, and vice versa, such that the tine members 141 are interdigitated. In other words, the tines 141, opposing grasping members 144, opposing interior surfaces 149 and intersecting arm members 111 and 112 may be analogized to human fingers, hands, palms and forearms.

The tonsil forceps of this second embodiment further comprise a plurality of interior projection members 146 positioned on the interior surfaces 149 of the grasping members 144, the interior projection members 146 being blunt structural features, such as raised ridges, mounds, posts or the like which will abut the sides of the tonsil but not penetrate or cut into its surface when the forceps are closed around the tonsil. The height and positioning of the opposing interior projections 146 are such that the interior projection members 146 of the first intersecting arm member 111 do not contact the interior projection members 146 of the second intersecting arm member 112 when the forceps are in the fully closed position.

The interior surface 149 of each of the grasping members 144 is bounded by a convex-side lateral edge 153 on the convex side 151 and by a concave-side lateral edge 154 on the concave side. At least one and preferably two flush lateral projection members 147 are disposed on or adjacent the concave-side lateral edge 154 of each grasping member 144, the flush lateral projection members 147 being substantially pointed or sharp and oriented generally perpendicularly to the interior surface 149, such that the flush lateral projection members 147 of one grasping member 144 extend directly toward the opposing flush lateral projection members 147 of the other grasping member 144 and do not extend outwardly or laterally from the concave-side lateral edge 154 or the concave side 152. In other words, the flush lateral projection members 147 are flush with the concave side 152 and are oriented at about a 90 degree angle to the interior surface 149.

At least one and preferably two angled lateral projection members 148 are disposed on or adjacent the convex-side lateral edge 153 of each grasping member 144, the angled lateral projection members 148 being substantially pointed or sharp and oriented slightly outwardly from the interior surface 149, such that the angled lateral projection members 148 extend outward laterally beyond the convex-side lateral edge 153 and the convex side 151. Preferably the angled lateral projection members 148 are oriented at about 135 degrees to the interior surface 149, but this angle may vary. The purpose of the angled lateral projection members 148 is to allow the surgeon to utilize the convex side 151 of the grasping members 144 to drag, roll or move the tonsil to better expose it for grasping, the outwardly extending angled lateral projection members 148 acting as short barbs to provide sufficient temporary securement to the surface of the tonsil for the surgeon to initiate movement of the tonsil.

A third and preferred embodiment of the tonsil forceps is illustrated in FIGS. 14 through 22. The structure and elements of the proximal portion of the tonsil forceps of this embodiment are identical or functionally similar to the proximal structure and elements of the second embodiment described herein. This preferred embodiment comprises first and second intersecting arm members 211 and 212 that are joined by pivoting connection means 220, such as a mechanical fastener 224 pivotally joining opposing intermediate body sections 221 in a manner that allows for scissor-type relative motion, the pivoting connection means 220 thereby defining a pivot plane. The portions of the first and second intersecting arm members 211 and 212 adjacent the distal end 214 of the tonsil forceps extend from the defined pivot plane, such that each of the first and second intersecting arm members have a convex side 251 and a concave side 252. In other words, with the tonsil forceps placed onto a planar surface, the distal portions of the first and second intersecting arm members 211 and 212 will angle upward and extend out of the planar surface. Most preferably, the convex side 251 possesses a relatively small angle or bend in relation to the angle or bend of the concave side 252, i.e., the convex side 251 bends or angles only slightly out of the pivot plane while the concave side 252 bends or angles out of the pivot plane to a much greater degree, such that the grasping members 244 grow wider in the distal direction.

The distal portions of the first and second intersecting arm members 211 and 212 extending from the pivot plane define the grasping means 240 which are comprised of grasping members 244, the grasping members 244 being relatively wide and thin in cross-section members that are curved out of the pivot plane. The opposing interior surfaces 249 of the grasping members 244 are concavely curved, such that an open tonsil-receiving area is defined between the opposing interior surfaces 249, and each opposing interior surface 249 is laterally bounded by a convex-side lateral edge 253 (i.e., a lateral edge located on the convex side 251) and a concave-side lateral edge 254 (i.e., a lateral edge located on the concave side 252). The lateral edges 253 and 254 may be straight, angled, curved or curvilinear. A plurality of relatively short teeth or tine members 241 separated by tine gaps 243 are positioned on the distal ends and extending around onto the convex-side lateral edge 253 of each of the grasping members 244. The tine members 241 and tine gaps 243 structured and disposed such that the tine members 241 of the first intersecting arm member 211 are positioned opposite from the gaps 212 of the second intersecting arm member 212, and the tine members 241 of the second arm member 212 are positioned opposite from the tine gaps 243 of the first arm member 211, such that the tine members 241 do not make contact when the tonsil forceps are closed, thereby precluding any shearing of the tonsil or surrounding tissue. The tine members 241 are not pointed or sharp, instead being provided with a blunt or substantially flat upper surface.

The tonsil forceps of this preferred embodiment further comprise a plurality of interior projection members 246 positioned on the interior surfaces 249 of the grasping members 244, the interior projection members 246 being blunt structural features, such as raised ridges or mounds, which will abut the sides of the tonsil but not penetrate or cut into its surface when the forceps are closed around the tonsil. The height and positioning of the opposing interior projections 246 are such that the interior projection members 246 of the first intersecting arm member 211 do not contact the interior projection members 246 of the second intersecting arm member 212 when the forceps are in the fully closed position. Furthermore, the interior projection members 246 are separated in order to produce and define projection gaps 245 between each of the interior projection members 246. As with the tine members 241, the interior projection members 246 of first arm member 211 are positionally offset from the interior projection members 246 of second arm member 212.

Figure 17:
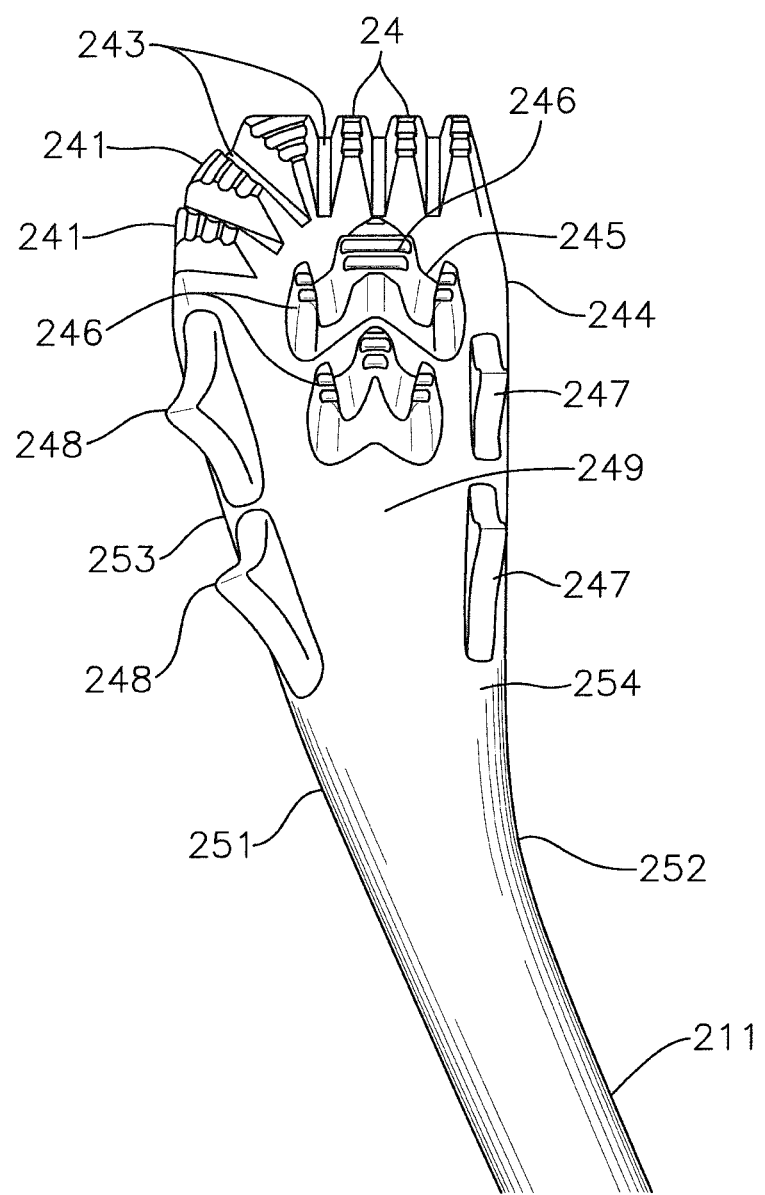
FIG. 17 is a partial view of the embodiment of FIG. 14 showing the inside of the grasping member of the first arm member.
Figure 18:
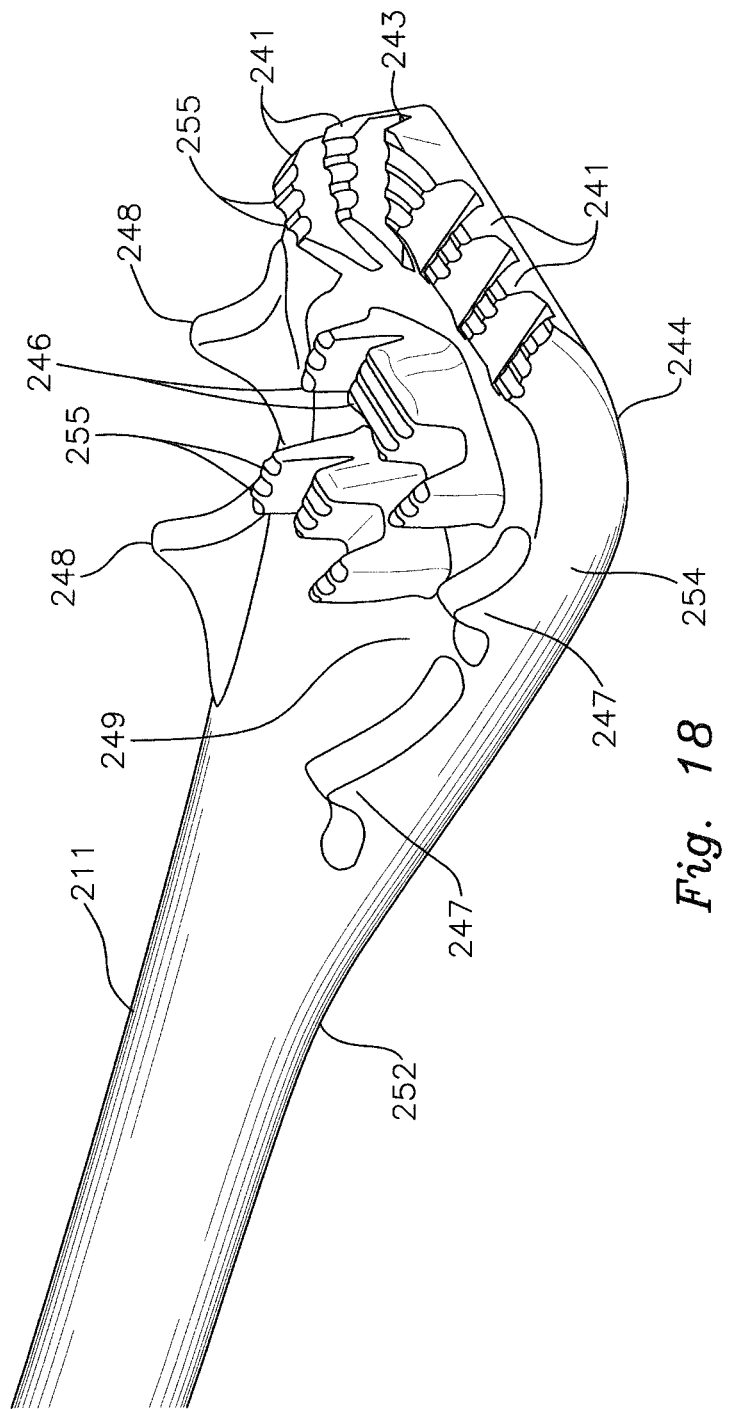
FIG. 18 is a partial view of grasping member of the first arm member of FIG. 17 shown from the concave side.
Figure 19:
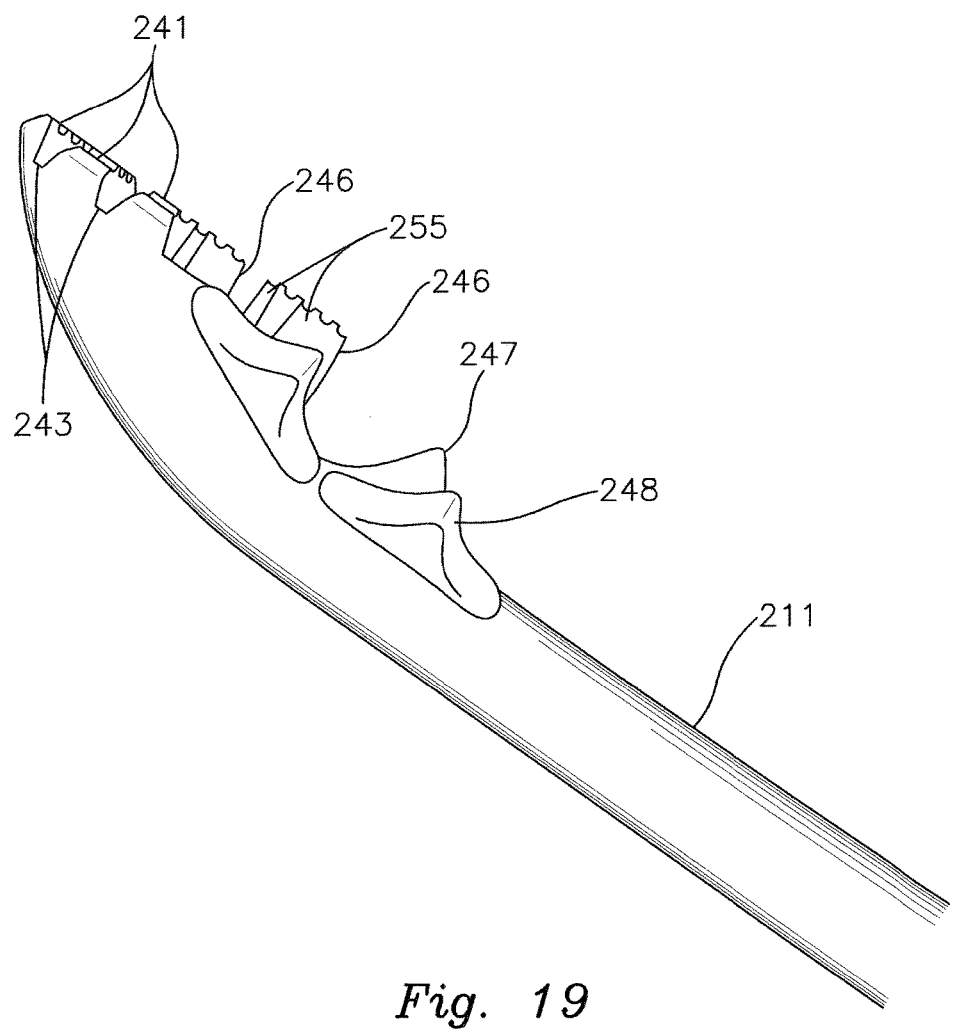
FIG. 19 is a partial lateral view of grasping member of the first arm member of FIG. 17 shown from the convex side.
Figure 20:
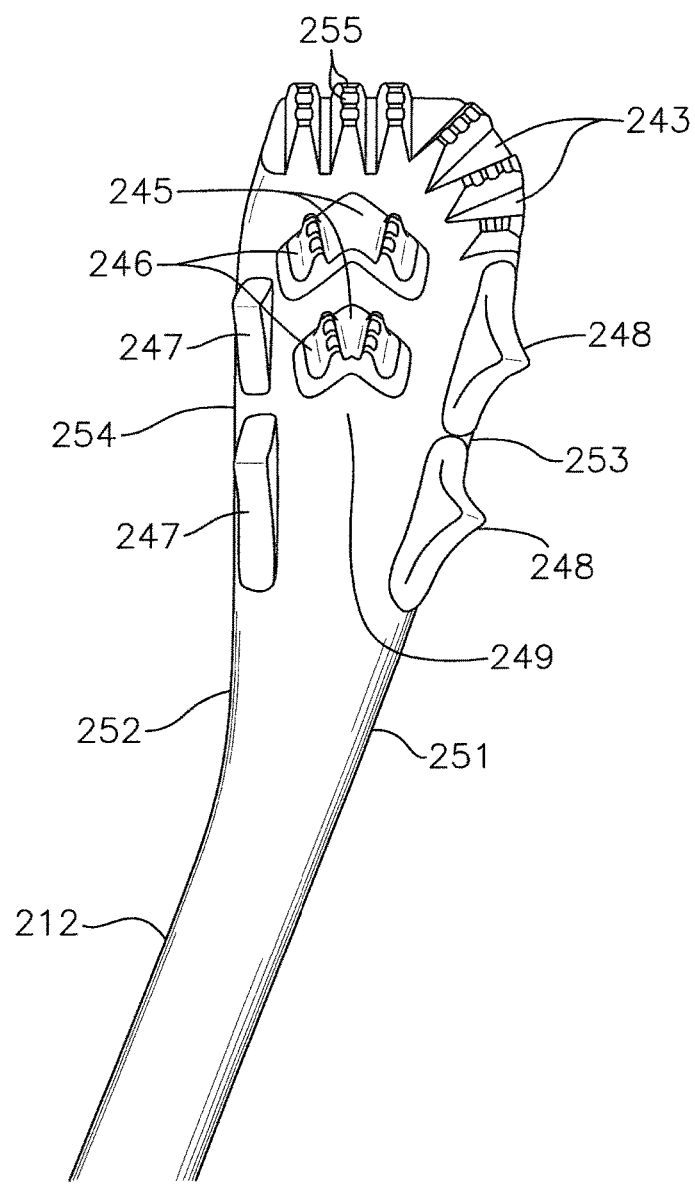
FIG. 20 is a partial view of the embodiment of FIG. 14 showing the inside of the grasping member of the second arm member.
Figure 21:
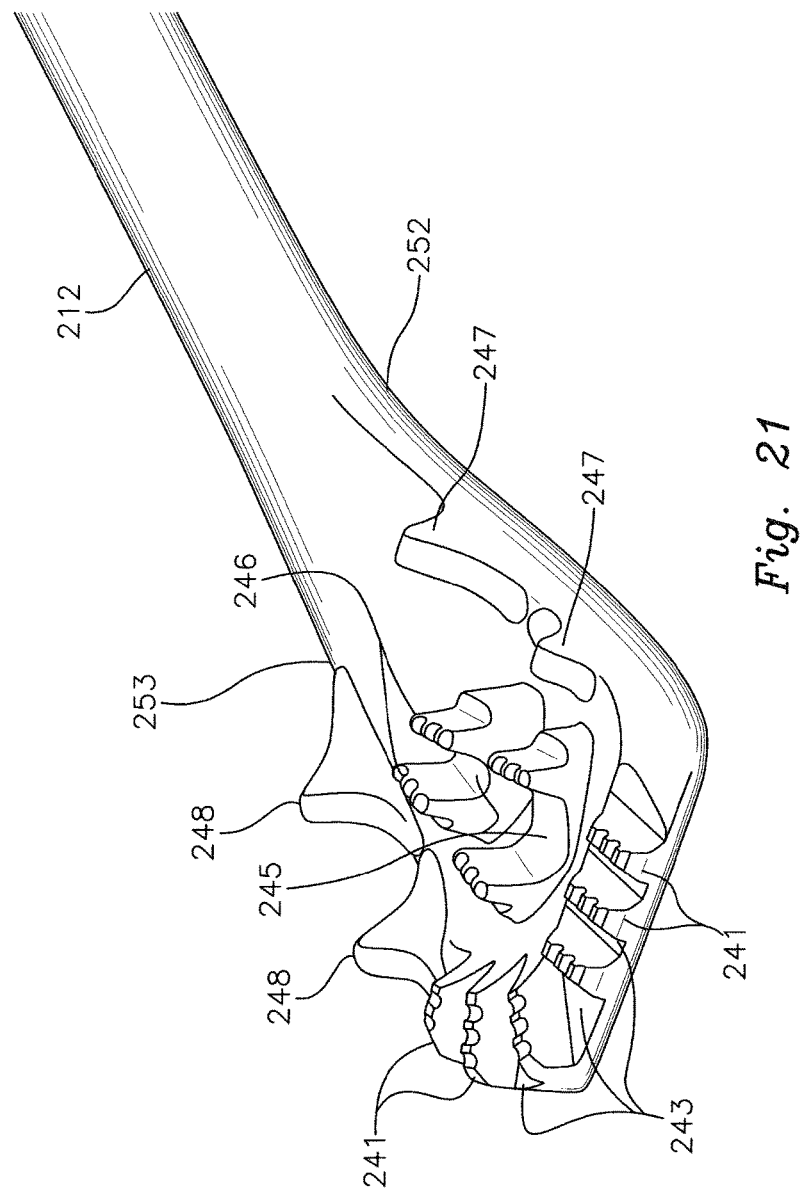
FIG. 21 is a partial view of grasping member of the first arm member of FIG. 20 shown from the concave side.
Figure 22:
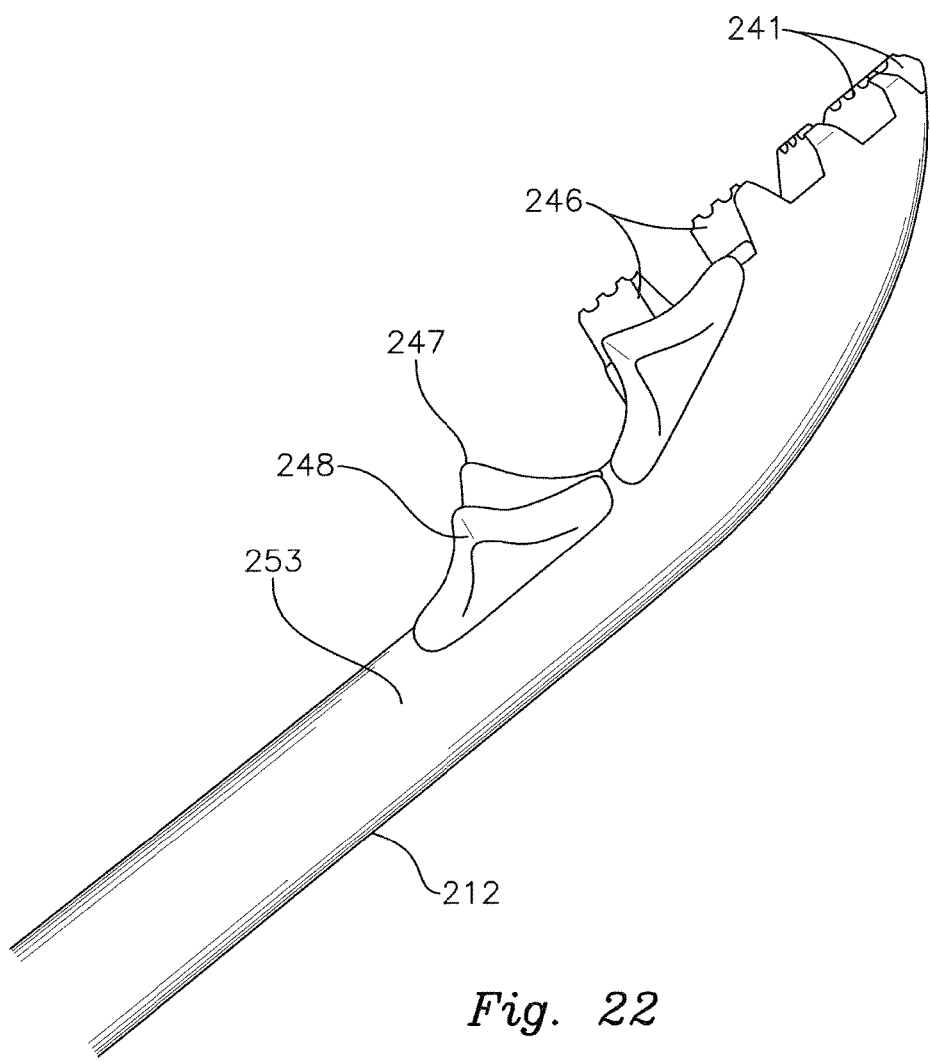
FIG. 22 is a partial lateral view of grasping member of the first arm member of FIG. 20 shown from the convex side.

In a preferred embodiment as shown in FIGS. 14 through 22, two laterally-extending sets of interior projection members 246 are provided on the interior opposing surfaces 149 of each grasping member 244. Each laterally-extending set of interior projection members 246 on first arm member 211 has three projection members 246, as shown in FIG. 17, and each laterally-extending set of interior projection members 246 on second arm member 212 has two projection members 246, as shown in FIG. 20. In this manner the interior projection members 246 of second arm member 212 extend toward and are aligned with the projection gaps 245 of first arm member 211. The middle one of each set of the interior projection members 246 of first arm member 211 extends toward and are aligned with the central projection gaps 245 of second arm member 212, and the outer two of each set of the interior projection members 246 on second arm member 212 are aligned to the outside of each set of the interior projection members 246 on first arm member 211.

In a preferred embodiment, the interior projection members 246 in each set are arranged in a forward-oriented V-shape, with the distal set of interior projection members 246 extending laterally farther than the proximal set of projection members 246. The middle projection member 246 of the first arm member is wider than the outer projection members 246 and is positioned distally ahead of the outer projection members 246, as shown in FIG. 17. The projection gaps 245 angle outwardly from the midline in the distal direction and are oriented such that the projection gaps 245 of the distal set of are aligned with the corresponding projection gaps 245 of the proximal set. The projection gap 245 of the second arm member 212 corresponds generally to the shape of the middle projection member 246 of the first arm member 211, such that it widens in the distal direction, as shown in FIG. 20. The projection members 246 of the second arm member 212 angle outwardly from the midline in the distal direction and are oriented such that the projection members 246 of the distal set are aligned with the corresponding projection members 246 of the proximal set Likewise, the projection members 246 of the second arm member 212 correspond generally to the shape of the projection gaps 245 of the first arm member 211. The outer surfaces of the interior projection members 246, as well as the ends of the tine members 241, are preferably provided with rough surfaces to better grip the tonsil, such as for examples laterally-extending ridges 255. The outer surfaces of the interior projection members 246 and the ends of the tine members 241 of each grasping member 244 are preferably disposed at the same height, i.e., reside in a single plane.

The interior surface 249 of each of the grasping members 244 is bounded by a convex-side lateral edge 253 on the convex side 251 and by a concave-side lateral edge 254 on the concave side. At least one and preferably two flush lateral projection members 247 are disposed on or adjacent the concave-side lateral edge 254 of each grasping member 244, the flush lateral projection members 247 being substantially pointed or sharp and oriented generally perpendicularly to the interior surface 249, such that the flush lateral projection members 247 of one grasping member 244 extend directly toward the opposing flush lateral projection members 247 of the other grasping member 244 and do not extend outwardly or laterally from the concave-side lateral edge 254 or the concave side 252. In other words, the flush lateral projection members 247 are flush with the concave side 252 and are oriented at about a 90 degree angle to the interior surface 249.

At least one and preferably two angled lateral projection members 248 are disposed on or adjacent the convex-side lateral edge 253 of each grasping member 244, the angled lateral projection members 248 being substantially pointed or sharp and oriented slightly outwardly from the interior surface 249, such that the angled lateral projection members 248 extend outward laterally beyond the convex-side lateral edge 253 and the convex side 251. Preferably the angled lateral projection members 248 are oriented at about 135 degrees to the interior surface 249, but this angle may vary. The purpose of the angled lateral projection members 248 is to allow the surgeon to utilize the convex side 251 of the grasping members 244 to drag, roll or move the tonsil to better expose it for grasping, the outwardly extending angled lateral projection members 248 acting as short barbs to provide sufficient temporary securement to the surface of the tonsil for the surgeon to initiate movement of the tonsil.

The particular combination of elements as described in the third and preferred embodiment optimizes the functionality of the tonsil forceps by reducing the likelihood that tissue will be shredded or torn rather than being securely grasped by the tonsil forceps. Aligning the tine members 241 and the interior projection members 246 of one grasping member 244 in offset manner relative to the tine members 241 and the interior projection members 246 of the other grasping member 244, as well as wrapping the tine members 241 around the distal ends of the grasping members 244 onto the convex sides 251 precludes undesirable shearing around and on the body of the tonsil. Positioning the angled lateral projection members 248 on the convex sides of the grasping members 244 allows the angled lateral projection members 248 to be used to move tissue.

It is contemplated that equivalents and substitutions for elements set forth above may be obvious to one of ordinary skill in the art, and therefore the true scope and definition of the invention is to be as set forth in the following claims.

I claim:

1. A tonsil forceps comprising:
a first intersecting arm member and a second intersecting arm member, each having a distal end and a proximal end, said arm members being joined by pivoting connection means defining a pivot plane, such that said distal ends can be closed and opened by bringing together or spreading apart said arm member proximal ends in a scissor-like manner, said distal ends of said arm members extending out of said pivot plane such that each said arm member has a concave side and a convex side;
a finger loop positioned at said proximal end of each said arm member;
means for temporarily locking said forceps in a fixed position;
each said first and said second arm members comprising a tonsil grasping member, each said grasping member comprising an interior surface bounded by a convex-side lateral edge and a concave-side lateral edge, tine members positioned on said distal end and extending around onto said convex-side lateral edge of each grasping member, tine gaps disposed between said tine members, inwardly facing, interior projection members positioned on each of said interior surfaces, and projection gaps disposed between said interior projection members;
wherein said tine members of said first arm member are positioned opposite from said tine gaps of said second arm member and said tine members of said second arm member are positioned opposite said tine gaps of said first arm member, such that said tine members do not contact each other when said forceps are closed;
wherein said interior projection members of said first arm member are positioned opposite from said projection gaps of said second arm member and said interior projection members of said second arm member are positioned opposite said projection gaps of said first arm member, such that said interior projection members do not contact each other when said forceps are closed; and
each said grasping member further comprising at least one flush lateral projection member disposed on or adjacent said concave-side lateral edge and at least one angled lateral projection member disposed on or adjacent said convex-side lateral edge, whereby said at least one flush lateral projection member is flush with said concave side and said at least one angled projection member extends outwardly from said convex side.

2. The forceps of claim 1, wherein said tine members comprise flat surfaces with ridges.

3. The forceps of claim 2, wherein on said first arm member, the flat surfaces of said tine members and said interior projection members lie in the same plane, and wherein on said second arm member, the flat surfaces of said tine members and said interior projection members lie in the same plane.

4. The forceps of claim 1, wherein said interior projection members comprise flat surfaces with ridges.

5. The forceps of claim 4, wherein said tine members comprise flat surfaces with ridges.

6. The forceps of claim 1, wherein said interior projection members are provided in two laterally-extending sets on each said grasping member, one said set being a distal set and the other said set being a proximal set.

7. The forceps of claim 6, wherein each said set of said interior projection members positioned on said first arm member comprises three interior projection members and two projection gaps, and wherein each said set of said interior projection members positioned on said second arm member comprises two interior projection members and one projection gap.

8. The forceps of claim 7, wherein each said set of said interior projection members positioned on said first arm member is V-shaped.

9. The forceps of claim 7, wherein each of said projection gaps of each said distal set of said interior projection members on said first arm member align with said projection gaps of each said proximal set of interior projection members.

10. The forceps of claim 9, wherein each said set of said interior projection members on said first arm member comprises two outer interior projection members and a middle interior projection member; wherein the middle interior projection member of each said set of said interior projection members on said first arm member is wider than the outer interior projection members of each said set of said interior projection members on said first arm member.

11. The forceps of claim 1, wherein each of said flush lateral projection members extend approximately 90 degrees from said interior surface and each of said angled lateral projection members extend approximately 135 degrees from said interior surface.

12. The forceps of claim 1, wherein each of said flush lateral projection members and each of said angled lateral projection members are pointed.

13. A tonsil forceps comprising:
a first intersecting arm member and a second intersecting arm member, each having a distal end and a proximal end, said arm members being joined by pivoting connection means defining a pivot plane, such that said distal ends can be closed and opened by bringing together or spreading apart said arm member proximal ends in a scissor-like manner, said distal ends of said arm members extending out of said pivot plane such that each said arm member has a concave side and a convex side;
a finger loop positioned at said proximal end of each said arm member;
means for temporarily locking said forceps in a fixed position;
each said first and said second arm members comprising a tonsil grasping member, each said grasping member comprising an interior surface bounded by a convex-side lateral edge and a concave-side lateral edge, flat surfaced tine members positioned on said distal end and extending around onto said convex-side lateral edge of each grasping member, tine gaps disposed between said tine members, inwardly facing, flat surfaced interior projection members positioned on each said interior surfaces, and projection gaps disposed between said interior projection members;
wherein said tine members of said first arm member are positioned opposite from said tine gaps of said second arm member and said tine members of said second arm member are positioned opposite said tine gaps of said first arm member, such that said tine members do not contact each other when said forceps are closed;
wherein said interior projection members of said first arm member are positioned opposite from said projection gaps of said second arm member and said interior projection members of said second arm member are positioned opposite said projection gaps of said first arm member, such that said interior projection members do not contact each other when said forceps are closed; and
each said grasping member further comprising at least one flush lateral projection member disposed on or adjacent said concave-side lateral edge and at least one angled lateral projection member disposed on or adjacent said convex-side lateral edge, whereby said at least one flush lateral projection member is flush with said concave side and said at least one angled projection member extends outwardly from said convex side, said at least one flush lateral projection member and said at least one angled lateral projection member being pointed.

14. The forceps of claim 13, wherein said tine members and said interior projection members comprise ridges.

15. The forceps of claim 13, wherein on said first aiiii member, the flat surfaces of said tine members and said interior projection members lie in the same plane, and wherein on said second arm member, the flat surfaces of said tine members and said interior projection members lie in the same plane.

16. The forceps of claim 13, wherein each of said flush lateral projection members extend approximately 90 degrees from said interior surface and each of said angled lateral projection members extend approximately 135 degrees from said interior surface.

17. The forceps of claim 13, wherein on said first arm member, the flat surfaces of said tine members and said interior projection members lie in the same plane, and wherein on said second arm member, the flat surfaces of said tine members and said interior projection members lie in the same plane.

18. The forceps of claim 16, wherein said interior projection members are provided in two laterally-extending sets on each said grasping member, one said set being a distal set and the other said set being a proximal set;
wherein each said set of said interior projection members positioned on said first arm member comprises three interior projection members and two projection gaps, and wherein each said set of said interior projection members positioned on said second arm member comprises two interior projection members and one projection gap;
wherein each said set of said interior projection members positioned on said first arm member is V-shaped; and
wherein each of said projection gaps of each said distal set of said interior projection members on said first arm member align with said projection gaps of each said proximal set of interior projection members.

19. The forceps of claim 18, wherein each said set of said interior projection members on said first arm member comprises two outer interior projection members and a middle interior projection member; wherein the middle interior projection member of each said set of said interior projection members on said first arm member is wider than the outer interior projection members of each said set of said interior projection members on said first arm member.

20. A tonsil forceps comprising:
a first intersecting arm member and a second intersecting arm member, each having a distal end and a proximal end, said arm members being joined by pivoting connection means defining a pivot plane, such that said distal ends can be closed and opened by bringing together or spreading apart said arm member proximal ends in a scissor-like manner, said distal ends of said arm members extending out of said pivot plane such that each said arm member has a concave side and a convex side;
a finger loop positioned at said proximal end of each said arm member;
means for temporarily locking said forceps in a fixed position;
each said first and said second arm members comprising a tonsil grasping member, each said grasping member comprising an interior surface bounded by a convex-side lateral edge and a concave-side lateral edge, flat surfaced tine members positioned on said distal end and extending around onto said convex-side lateral edge of each grasping member, tine gaps disposed between said tine members, inwardly facing, flat surfaced interior projection members positioned on each of said interior surfaces, and projection gaps disposed between said interior projection members;

wherein said tine members of said first arm member are positioned opposite from said tine gaps of said second arm member and said tine members of said second arm member are positioned opposite said tine gaps of said first arm member, such that said tine members do not contact each other when said forceps are closed;

wherein on said first arm member, the flat surfaces of said tine members and said interior projection members lie in the same plane, and wherein on said second arm member, the flat surfaces of said tine members and said interior projection members lie in the same plane;

wherein said interior projection members of said first arm member are positioned opposite from said projection gaps of said second arm member and said interior projection members of said second arm member are positioned opposite said projection gaps of said first arm member, such that said interior projection members do not contact each other when said forceps are closed;

wherein said interior projection members are provided in two laterally-extending sets on each said grasping member, one said set being a distal set and the other said set being a proximal set;

wherein each said set of said interior projection members positioned on said first arm member comprises three interior projection members, two of said three interior projection members being outer interior projection members and one of said three interior projection members being a middle interior projection member, and two projection gaps, and wherein each said set of said interior projection members positioned on said second arm member comprises two interior projection members and one projection gap;

wherein each said set of said interior projection members positioned on said first arm member is V-shaped; and wherein each of said projection gaps of each said distal set of said interior projection members on said first arm member align with said projection gaps of each said proximal set of interior projection members;

wherein the middle interior projection member of each said set of said interior projection members on said first arm member is wider than the outer interior projection members of each said set of said interior projection members on said first arm member; and each said grasping member further comprising at least one flush lateral projection member disposed on or adjacent said concave-side lateral edge and at least one angled lateral projection member disposed on or adjacent said convex-side lateral edge, whereby said at least one flush lateral projection member is flush with said concave side and said at least one angled projection member extends outwardly from said convex side, said at least one flush lateral projection member and said at least one angled lateral projection member being pointed, and wherein said flush lateral projection members extend approximately 90 degrees from said interior surface and said angled lateral projection members extend approximately 135 degrees from said interior surface.

* * * * *